(12) United States Patent
Wang et al.

(10) Patent No.: US 6,863,778 B2
(45) Date of Patent: Mar. 8, 2005

(54) SEPARATION OF TERTIARY BUTYL ALCOHOL FROM DIISOBUTYLENE

(75) Inventors: Jianhua Wang, Sugar Land, TX (US); Nishit Sahay, Houston, TX (US); Mitchell E. Loescher, Houston, TX (US); Montri Vichailak, Houston, TX (US)

(73) Assignee: Catalytic Distillation Technologies, Pasadena, TX (US)

(*) Notice: Subject to any disclaimer, the term of this patent is extended or adjusted under 35 U.S.C. 154(b) by 287 days.

(21) Appl. No.: 10/314,537

(22) Filed: Dec. 9, 2002

(65) Prior Publication Data

US 2004/0020758 A1 Feb. 5, 2004

Related U.S. Application Data

(60) Provisional application No. 60/398,498, filed on Jul. 25, 2002.

(51) Int. Cl.[7] .............................. B01D 3/36; B01D 3/42; C07C 7/06
(52) U.S. Cl. ................................ 203/2; 203/3; 203/78; 203/80; 203/99; 203/DIG. 19; 585/510; 585/520; 585/639; 568/913
(58) Field of Search .......................... 203/2, 3, 99, 78, 203/80, 71, 63, 73, DIG. 19; 585/510, 520, 639, 649, 832, 501; 568/913

(56) References Cited

U.S. PATENT DOCUMENTS

| | | | |
|---|---|---|---|
| 4,100,220 A | 7/1978 | Bowman et al. | 260/683.15 R |
| 4,313,016 A | 1/1982 | Manning | 585/832 |
| 4,336,407 A * | 6/1982 | Smith, Jr. | 568/697 |
| 4,469,911 A | 9/1984 | Manning | 585/515 |
| 5,600,024 A | 2/1997 | Eldridge et al. | 568/697 |
| 5,811,620 A | 9/1998 | Knifton et al. | 585/639 |
| 5,866,714 A * | 2/1999 | Szady et al. | 560/247 |
| 5,877,372 A | 3/1999 | Evans et al. | 585/510 |
| 6,011,191 A | 1/2000 | Di Girolamo et al. | 585/514 |
| 6,166,270 A * | 12/2000 | Gupta et al. | 568/877 |
| 6,274,783 B1 * | 8/2001 | Gildert et al. | 585/255 |
| 6,376,731 B1 | 4/2002 | Evans et al. | 585/510 |
| 6,433,238 B1 | 8/2002 | Di Girolamo et al. | 585/510 |

* cited by examiner

Primary Examiner—Virginia Manoharan
(74) Attorney, Agent, or Firm—Kenneth H. Johnson

(57) ABSTRACT

A process for the separation of diisobutylene from tertiary butyl alcohol utilizing pressure swing azeotropic distillation to achieve the desired separation. The pressure swing azeotropic distillation takes advantage of the fact that different azeotropes are formed at different pressures. Isobutylene in $C_4$ streams is oligomerized in the presence of tertiary butyl alcohol to produce the diisobutylene. Tertiary butyl alcohol is present in the dimerization because it improves the selectivity to the dimer (diisobutylene) by suppressing further reaction to the trimer or higher. The diisobutylene is separated from the tertiary butyl alcohol utilizing two distillation columns. The first distillation is operated at a higher pressure than the second such that the minimum boiling azeotropes of tertiary butyl alcohol and diisobutylene have different concentrations of tertiary butyl alcohol. Diisobutylene is removed as bottoms from the first distillation column and unreacted C4's are removed as overheads at 60–130 psig. A side draw containing the minimum boiling azeotrope is fed to the second distillation column, operated at 0–45 psig where a second minimum boiling azeotrope is formed having a lower tertiary butyl alcohol concentration. The tertiary butyl alcohol is recovered as bottoms and recycled to the reactor. The second minimum boiling azeotrope is removed as overheads and recycled to the first distillation column.

9 Claims, 2 Drawing Sheets

SEPARATION OF TERTIARY BUTYL ALCOHOL FROM DIISOBUTYLENE

RELATED APPLICATION

This application claims priority of U.S. Provisional Patent Application Ser. No. 60/398,498 filed Jul. 25, 2002.

BACKGROUND OF THE INVENTION

1. Field of the Invention

The present invention relates to a process for separating tertiary butyl alcohol from diisobutylene. More particularly the invention relates to a process utilizing pressure swing azeotrope distillation wherein two distillation columns are operated at different pressures to achieve the separation.

2. Related Information

Isobutylene is dimerized to diisobutylene according to the following reaction:

(1) Isobutylene+Isobutylene⇌Diisobutylenes     (1)

The dimerization of isobutylene with itself is of particular interest because either of the isomers of diisobutylene produce 2,2,4-trimethyl pentane (isooctane) when hydrogenated. The dimerization catalyst may include either an acidic cation exchange resin or zeolite. The dimerization of isobutylene over an acid catalyst in the presence of tertiary butyl alcohol is disclosed in U.S. Pat. No. 4,100,220.

Diisobutylene is an important oligomerization product useful for hydrogenation to isooctane. In one process isobutylene is oligomerized in the presence of tertiary butyl alcohol to produce the diisobutylene. Conversion of olefins to gasoline and/or distillate products is disclosed in U.S. Pat. Nos. 3,960,978 and 4,021,502 wherein gaseous olefins in the range of ethylene to pentene either alone or in admixture with paraffins are converted into an olefinic gasoline blending stock by contacting the olefins with a catalyst bed made up of a ZSM-5 type zeolite. The presence of tertiary butyl alcohol improves the selectivity to the dimer (diisobutylene) by suppressing further reaction to the trimer or higher. The tertiary butyl alcohol is then separated and recycled back to the oligomerization reactor. A process utilizing such a concept is disclosed in U.S. Pat. No. 4,100,220. However, diisobutylene forms a minimum boiling azeotrope with tertiary butyl alcohol rendering separation difficult. One common method of separating the two in the past has been by extractive distillation wherein a solvent or third component is introduced into the mixture to lower the relative volatility of one of the components. The draw back to this method is that a third component is used which itself must be separated from one of the two primary components.

It is an advantage of the present invention that the treatment of a product stream containing DIB and TBA with a third stream is avoided. It is a feature of the present invention that the TBA is recovered from a debutanizer DIB/TBA azeotrope by a separate lower pressure fractionation.

SUMMARY OF THE INVENTION

Briefly the present invention utilizes pressure swing azeotropic distillation to achieve the desired separation. The pressure swing azeotropic distillation takes advantage of the fact that different azeotropes are formed at different pressures.

The feed to the dimerization will generally comprise from 5 to 100 mole % isobutylene, such as a stream containing normal butenes, isobutene and butanes or $C_3$ to $C_5$ hydrocarbons. Usually there will be other components, such as butene-1, butene-2, normal butane and isobutane and the isobutylene will comprise from 9 to 60 mole % of the feed to the dimerization. Small amounts of $C_3$'s and $C_5$'s are usually present. The dimerization product will generally contain from about 10 to 50 mole % unreacted $C_4$'s, which needs to be separated and recovered from the DIB and the TBA.

A first distillation column is operated at a first pressure with the first azeotrope being maintained within the column above the bottom and below the overheads. Unreacted $C_4$'s (mostly butenes) are taken overheads and essentially pure diisobutylene is removed as bottoms. A side draw of the azeotrope is fed to a second distillation column operated at a lower pressure than the first. The azeotrope in the second column is lower in tertiary butyl alcohol concentration than in the first column and thus essentially pure tertiary butyl alcohol can be removed as bottoms. The overheads, comprising an azeotrope having a lower tertiary butyl alcohol concentration is then fed back to the first column. The tertiary butyl alcohol bottoms from the second column is then recycled back to the oligomerization reactor.

In the normal course of producing DIB, from C4 cuts there may be substantial amounts of unreacted materials in the $C_4$ hydrocarbon range to be separated from the DIB in addition to the TBA, thus a debutanizing step is often carried out to recover the DIB. The pressure conditions for the debutanization may be in the range of 60–130 psig for this separation while maintaining the DIB/TBA azeotrope in the column, where it can be removed as a side draw, taken to a separate column and fractionated at a lower pressure, e.g., in the range of 0–45 psig, where there is a different azeotrope for DIB and TBA, which allows further separation and recovery of the TBA.

DETAILED DESCRIPTION OF THE PREFERRED EMBODIMENT

Figure 1:
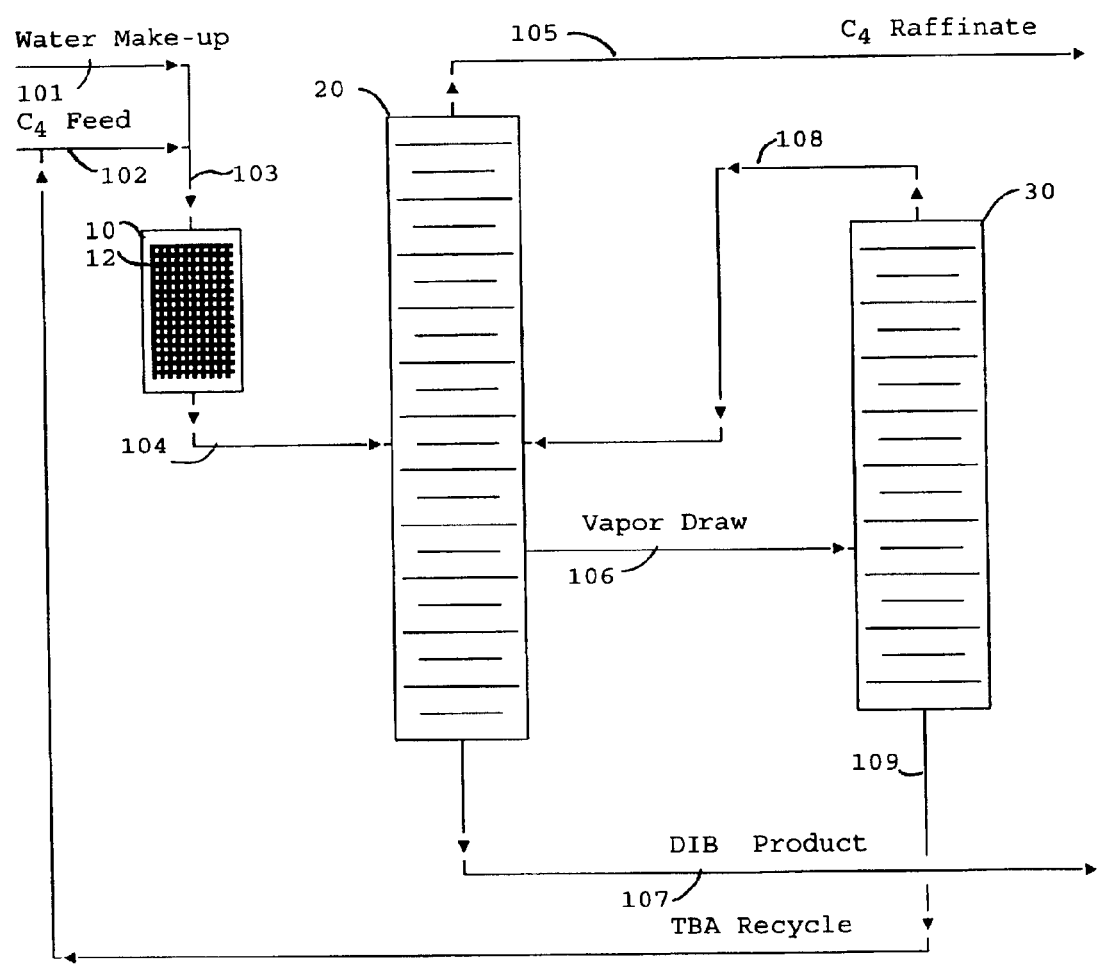
FIG. 1 is a flow diagram in schematic form of one embodiment of the invention.

Referring now to FIG. 1 there is shown a flow diagram in schematic form of the preferred embodiment of the invention. A mixed $C_4$ stream containing isobutylene, butenes, butane, isobutane and heavier compounds is combined with a TBA stream which is recycled from the process via flow line 109 and the combined stream fed via flow line 102. Water is fed via line 101 and is combined with the mixture in flow line 103 and fed to reactor 10 containing a bed 12 of oligomerization catalyst such as Amberlyst 15 acidic cation exchange resin. The water is added to produce tertiary butyl alcohol from reaction with isobutylene. The amount of water must be carefully controlled to less than about 0.06 mole per mole of isobutylene or the hydration reaction will become predominant. The tertiary butyl alcohol (TBA) suppresses the dimerization slightly, however it is a substantial benefit in suppressing the production of trimer, higher polymers and codimers. The remainder of the isobutylene reacts with itself in the reactor 10 to form diisobutylene (DIB).

The effluent from the reactor 10 is taken via flow line 104 and fed to a first distillation column 20 which is operated at a first pressure P1. The TBA and DIB form a minimum boiling azeotrope in the column which can be maintained above the bottom draw and essentially pure DIB can be withdrawn via flow line 107. The unreacted $C_4$'s (mostly butane and butenes) being lower boiling than the minimum boiling azeotrope are withdrawn as overheads via flow 105 as $C_4$ raffinate.

Either a liquid or vapor draw is taken from the tray where the minimum boiling azeotrope is maintained and fed via flow line 106 to a second distillation column 30 which is operated at a second pressure P2 which is lower than P1, the pressure in the first distillation column 20. Although the vapor draw is more preferable since the concentration of TBA will be slightly higher than that of the liquid and a vapor provides lower energy consumption for column 30, the liquid draw is much easier in terms of flow control and design. The lower pressure creates a second minimum azeotrope of TBA and DIB except the concentration of TBA is lower than in the first distillation column 20 allowing essentially pure TBA to be withdrawn as bottoms via flow line 109 and recycled to reactor 10. The second minimum boiling azeotrope is taken as overheads and fed back to the first distillation column via flow line 108.

Figure 2:
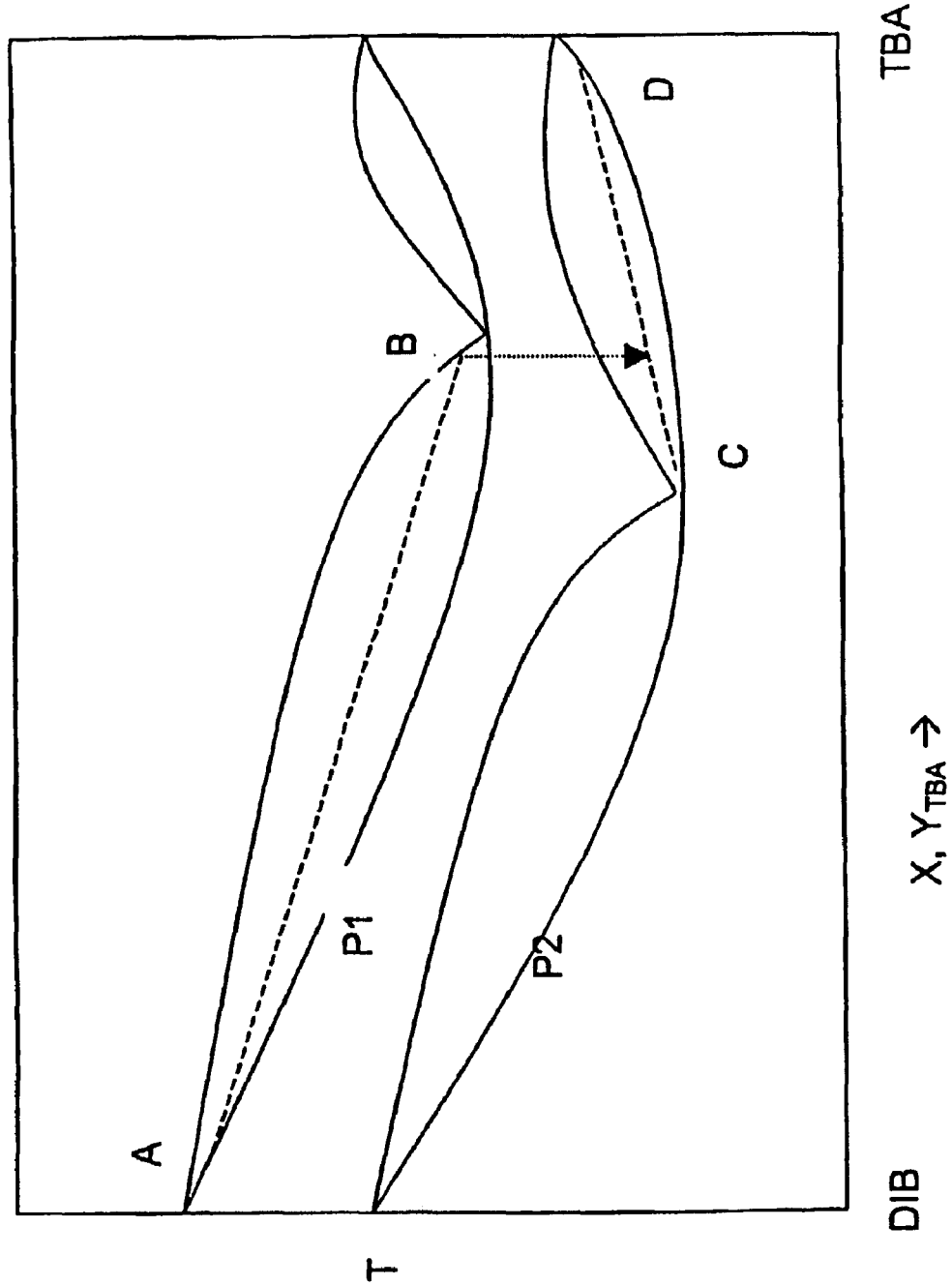
FIG. 2 is graphical representation of the effect of pressure on the concentrations of diisobutylene and tertiary butyl alcohol as a function of temperature for two different pressures.

The system is graphically depicted in FIG. 2 wherein compositions of DIB-TBA in the vapor and liquid phases are plotted as a function of temperature. The concentration of TBA increases toward the right of the graph. The top graph is the plot at P1 the higher pressure of the first distillation column. The DIB is withdrawn at point A with point B being the vapor draw from the first column which is fed to the second distillation column. The second, lower graph represents the plot at P2 the lower pressure of the second distillation column. Point C represents the overheads from the second column having the second minimum boiling azeotrope while point D represents the bottoms of the second column which is essentially pure TBA. Basically the first minimum boiling azeotrope boils at a lower temperature than pure DIB and higher than the C4's such that the first can be removed as bottoms while the second can be removed as overheads. The second minimum azeotrope boils at a temperature lower than the boiling point of TBA allowing TBA to be removed as bottoms with the minimum boiling azeotrope being taken as overheads to be recycled to the first distillation column.

EXAMPLE

In the example the first distillation column is operated at 72 to 116 psig and the second distillation column is operated at 0 to 45 psig. A material balance is shown below in Table I. The Stream Numbers match those in FIG. 1.

TABLE 1

| | Stream No. | | | | | | |
|---|---|---|---|---|---|---|---|
| | 103 | 104 | 105 | 106 | 107 | 108 | 109 |
| Temp., ° F. | 140 | 166.5 | 127.9 | 218.6 | 388.0 | 110.6 | 210.7 |
| Pressure, psig | 130.3 | 123.1 | 81.0 | 92.9 | 94.1 | 9.3 | 13.3 |
| Composition, mol % | | | | | | | |
| Propylene | 0.7 | 0.7 | 0.8 | 0.0 | 0.0 | 0.0 | 0.0 |
| Propane | 0.8 | 0.8 | 0.9 | 0.0 | 0.0 | 0.0 | 0.0 |
| Isobutane | 26.7 | 28.6 | 31.0 | 0.0 | 0.0 | 0.0 | 0.0 |
| Isobutylene | 20.1 | 8.6 | 9.3 | 0.0 | 0.0 | 0.0 | 0.0 |
| 1-Butene | 15.1 | 15.7 | 16.9 | 0.0 | 0.0 | 0.0 | 0.0 |
| 1,3 Butadiene | 0.4 | 0.4 | 0.5 | 0.0 | 0.0 | 0.0 | 0.0 |
| n-Butane | 9.7 | 10.4 | 11.3 | 0.2 | 0.0 | 0.2 | 0.0 |
| trans-2-Butene | 15.1 | 15.8 | 17.1 | 0.3 | 0.0 | 0.3 | 0.0 |
| cis-2-Butene | 10.0 | 10.4 | 11.3 | 0.4 | 0.0 | 0.4 | 0.0 |
| Isopentane | 0.8 | 0.8 | 0.8 | 78.6 | 1.1 | 87.2 | 0.0 |
| Water | 0.2 | 0.2 | 0.2 | 0.0 | 0.0 | 0.0 | 0.0 |
| TBA | 0.6 | 0.6 | 0.0 | 18.4 | 0.0 | 9.6 | 98.6 |
| DIB | 0.0 | 6.4 | 0.0 | 2.2 | 91.8 | 2.3 | 1.3 |
| Heavies | 0.0 | 0.5 | 0.0 | 0.0 | 7.1 | 0.0 | 0.0 |
| Total | 100.00 | 100.0 | 100.0 | 100.0 | 100.0 | 100.0 | 100.0 |

The invention claimed is:

1. A process for separating diisobutylene from tertiary butyl alcohol comprising the steps of:
   (a) feeding a stream comprising diisobutylene and tertiary butyl alcohol to a first distillation zone operated at a first pressure and under conditions to remove diisobutylene as a first bottoms and maintain a first azeotrope of diisobutylene and tertiary butyl alcohol within the first distillation zone above the bottoms but below the overheads;
   (b) withdrawing said first azeotrope from said first distillation zone; and
   (c) feeding said first azeotrope to a second distillation zone operated at a second pressure lower than said first pressure and under conditions to remove tertiary butyl alcohol as a second bottoms and taking a second azeotrope of diisobutylene and tertiary butyl alcohol as overheads, said second azeotrope having less tertiary butyl alcohol that said first azeotrope.

2. The process according to claim 1 wherein said second azeotrope are fed to said first distillation zone.

3. The process according to claim 1 wherein said stream contains $C_4$ hydrocarbons.

4. The process according to claim 3 wherein said first distillation zone is at a pressure in the range of 60–130 psig and said second distillation zone is at a pressure in the range of 0–45 psig.

5. The process according to claim 1 wherein said first distillation zone is at a pressure in the range of 60–130 psig and said second distillation zone is at a pressure in the range of 0–45 psig.

6. A process for the production of diisobutylene comprising the steps of:
   (a) feeding a stream comprising isobutylene and water to a reaction zone containing an acidic cation exchange resin wherein a portion of isobutylene reacts with water to form tertiary butyl alcohol and the remainder reacts with itself to form diisobutylene;
   (b) feeding the effluent from said reaction zone containing diisobutylene, tertiary butyl alcohol, butenes, and butanes to a first distillation zone operated at a first pressure wherein a first minimum boiling azeotrope of tertiary butyl alcohol and diisobutylene is formed, said first minimum boiling azeotrope boiling at a temperature below the boiling point of diisobutylene and above the boiling point of butenes and butanes;
   (c) removing diisobutylene from said first distillation zone as a first bottoms;
   (d) removing butenes and butane from said first distillation zone as a first overheads;
   (e) withdrawing a vapor side draw of said first minimum boiling azeotrope from said first distillation zone;
   (f) feeding said vapor side draw to a second distillation zone operated at a second pressure lower than said first pressure and operated such that a second minimum boiling azeotrope of tertiary butyl alcohol and diisobutylene is formed having a lower concentration of tertiary butyl alcohol than said first minimum boiling azeotrope, said second minimum boiling azeotrope boiling at a temperature below the boiling point of tertiary butyl alcohol;
   (g) removing tertiary butyl alcohol from said second distillation zone as a second bottoms;
   (h) removing said second minimum boiling azeotrope from said second distillation zone as a second overheads;
   (i) returning said second bottoms to said reaction zone; and
   (j) returning said second overheads to said first distillation zone.

7. The process according to claim 6 wherein said first distillation zone is at a pressure in the range of 60–130 psig and said second distillation zone is at a pressure in the range of 0–45 psig.

8. The process according to claim 6 wherein said stream comprises normal butenes, isobutene and butanes.

9. The process according to claim 6 wherein said stream comprises $C_3$ to $C_5$ hydrocarbons.

* * * * *